(12) United States Patent
Pizzoli et al.

(10) Patent No.: US 6,365,781 B2
(45) Date of Patent: Apr. 2, 2002

(54) PROCESS FOR THE PREPARATION OF MERCAPTOMETHYLPHENOIS

(75) Inventors: Fabio Pizzoli, Bologna (IT); Reto Luisoli, Hölstein (CH); Gerrit Knobloch, Magden (CH); Hans-Rudolf Meier, Fribourg (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/755,369

(22) Filed: Jan. 5, 2001

(30) Foreign Application Priority Data

Jan. 10, 2000 (EP) .............................. 00810020

(51) Int. Cl.[7] ............................................ C07C 319/00
(52) U.S. Cl. .............................. 568/52; 568/51; 568/58
(58) Field of Search .............................. 568/39, 51, 52, 568/57, 58

(56) References Cited

U.S. PATENT DOCUMENTS

| | | | |
|---|---|---|---|
| 3,553,270 A | * | 1/1971 | Wollensak et al. |
| 3,903,173 A | * | 9/1975 | Eggensperger et al. |
| 4,857,572 A | | 8/1989 | Meier et al. ............... 524/289 |
| 4,874,885 A | | 10/1989 | Stegmann et al. ............ 560/15 |
| 5,008,459 A | * | 4/1991 | Meier et al. |
| 5,276,258 A | | 1/1994 | Knobloch et al. .......... 524/114 |

OTHER PUBLICATIONS

CA:83:79881 abs of Azerb Khim Zh by Abdullaeva (5–6) pp 66–9, 1973.*
Langmuir, vol. 15, pp. 948–951 by Isabel Pastoriza–Santos et al, 1999.*
Chem. Abstr. 1990:425944 for JP 02042055 (1990).

* cited by examiner

*Primary Examiner*—Jean F. Vollano
(74) *Attorney, Agent, or Firm*—Kevin T. Mansfield

(57) ABSTRACT

There is disclosed an improved process for the preparation of a compound of the formula I

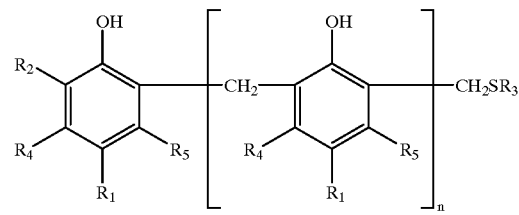

(I)

wherein n is 0 or 1, $R_1$ is $C_1$–$C_{12}$alkyl or —$CH_2SR_3$, $R_2$ is $C_1$–$C_{12}$alkyl, $C_7$–$C_9$phenylalkyl, $C_7$–$C_9$-phenylalkyl substituted on the phenyl radical by from 1 to 3 $C_1$–$C_4$alkyl groups; or —$CH_2SR_3$, $R_3$ is $C_6$–$C_{18}$alkyl, phenyl or benzyl, $R_4$ is hydrogen or methyl, $R_5$ is hydrogen or methyl, with the proviso that $R_4$ and $R_5$ are not simultaneously methyl, by reacting a compound of the formula II

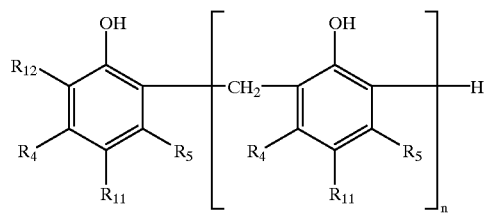

(II)

wherein n, $R_4$ and $R_5$ are as previously defined, $R_{11}$ is hydrogen or $C_1$–$C_{12}$alkyl; and $R_{12}$ is hydrogen, $C_1$–$C_{12}$alkyl, $C_7$–$C_9$phenylalkyl, $C_7$–$C_9$phenylalkyl substituted on the phenyl radical by from 1 to 3 $C_1$–$C_4$alkyl groups; with formaldehyde or a compound that liberates formaldehyde under the reaction conditions and with at least one compound of the formula III $$R_3SH \qquad (III)$$

wherein $R_3$ is as previously defined, in the presence of a base, said base being mono- or dimethylamine or mono- or diethylamine, which process comprises treating afterwards the reaction product with a reducing agent.

8 Claims, No Drawings

PROCESS FOR THE PREPARATION OF MERCAPTOMETHYLPHENOIS

The present invention relates to a new improved process for the preparation of mercaptomethylphenols from phenols by reaction with formaldehyde and mercaptans and which process comprises treating afterwards the reaction product with a reducing agent. The mercaptomethylphenols are valuable antioxidants for plastics, elastomers mineral oils and synthetic lubricants.

U.S. Pat. No. 4,857,572 discloses mercaptomethylphenols as antioxidants for plastics, elastomers, tackifying resins, mineral oils and lubricants.

U.S. Pat. No. 4,874,885 discloses a process for the preparation of mercaptomethylphenols from phenols by reaction with formaldehyde and mercaptans in the presence of mono-, di- or tri-methylamine or mono- or diethylamine.

U.S. Pat. No. 5,276,258 discloses that the stabilising properties of mercaptomethylphenols in elastomers can be improved by the additional use of an epoxidised fatty acid or fatty acid ester.

The mercaptomethylphenols prepared according to the known processes have the disadvantages that they for example possess an undesired smell and discolour in the presence of lithium catalysts or alkaline medium mainly because of the presence of undesired by-products or impurities.

The goal of the instant invention was therefore to find an improved process for the synthesis of mercaptomethylphenols with reduced smell, with reduced discoloration in the presence of for example lithium catalysts and alkaline medium, and with excellent storage stability.

Surprisingly, it has now been found that treating the crude mercaptomethylphenols prepared according to the process disclosed in U.S. Pat. No. 4,874,885 afterwards with a reducing agent improves the stabilizing qualitiy of the mercaptomethylphenols.

The present invention therefore relates to an improved process for the preparation of a compound of the formula I.

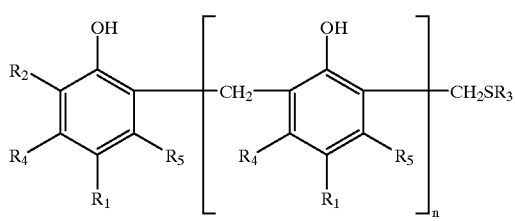

(I)

wherein n is 0 or 1, $R_1$ is $C_1$–$C_{12}$alkyl or —$CH_2SR_3$, $R_2$ is $C_1$–$C_{12}$alkyl, $C_7$–$C_9$phenylalkyl, $C_7$–$C_9$phenylalkyl substituted on the phenyl radical by from 1 to 3 $C_1$–$C_4$alkyl groups; or —$CH_2SR_3$, $R_3$ is $C_6$–$C_{18}$alkyl, phenyl or benzyl, $R_4$ is hydrogen or methyl, $R_5$ is hydrogen or methyl, with the proviso that $R_4$ and $R_5$ are not simultaneously methyl, by reacting a compound of the formula II

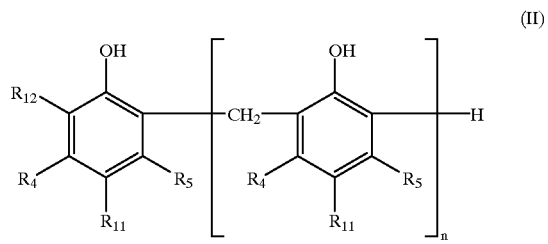

(II)

wherein n, $R_4$ and $R_5$ are as previously defined, $R_{11}$ is hydrogen or $C_1$–$C_{12}$alkyl; and $R_{12}$ is hydrogen, $C_1$–$C_{12}$alkyl, $C_7$–$C_9$phenylalkyl, $C_7$–$C_9$phenylalkyl substituted on the phenyl radical by from 1 to 3 $C_1$–$C_4$alkyl groups, with formaldehyde or a compound that liberates formaldehyde under the reaction conditions and with at least one compound of the formula III $$R_3SH \qquad (III)$$

wherein $R_3$ is as previously defined, in the presence of a base, said base being mono- or dimethylamine or mono- or diethylamine, which process comprises treating afterwards the reaction product with a reducing agent.

Alkyl having up to 18 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, tert-octyl, 2-ethylhexyl, 1,1,3-trimethylhexyl, 1,1,3,3-tetramethylpentyl, nonyl, decyl, undecyl, 1-methylundecyl, dodecyl, tridecyl, 1,1,3,3,5,5-hexamethylhexyl, tetradecyl, pentadecyl, hexadecyl, heptadecyl or octadecyl. One of the preferred definitions for $R_1$, $R_2$, $R_{11}$ and $R_{12}$ is $C_1$–$C_{12}$alkyl, especially preferred is $C_1$–$C_4$alkyl, for example methyl. A preferred definition for $R_3$ is $C_8$–$C_{12}$alkyl, for example, n-octyl or n-dodecyl.

$C_7$–$C_9$Phenylalkyl unsubstituted or substituted on the phenyl radical by from 1 to 3 $C_1$–$C_4$alkyl groups is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Preference is given to benzyl, α-methylbenzyl or α,α-dimethylbenzyl.

Of interest is a process for the preparation of a compound of formula I wherein, n is 0 or 1, $R_1$ is $C_1$–$C_4$alkyl or —$CH_2SR_3$, $R_2$ is $C_1$–$C_4$alkyl, $C_7$–$C_9$phenylalkyl, $C_7$–$C_9$phenylalkyl substituted on the phenyl radical by a methyl group, $R_3$ is $C_6$–$C_{12}$alkyl, $R_4$ is hydrogen or methyl, $R_5$ is hydrogen, $R_{11}$ is hydrogen or $C_1$–$C_4$alkyl; and $R_{12}$ is $C_1$–$C_4$alkyl, $C_7$–$C_9$phenylalkyl, $C_7$–$C_9$phenylalkyl substituted on the phenyl radical by a methyl group.

Likewise of interest is a process for the preparation of a compound of formula I wherein n is 0,
$R_1$ is —$CH_2SR_3$,
$R_2$ is $C_1$–$C_4$alkyl,
$R_3$ is $C_8$–$C_{12}$alkyl,
$R_4$ is hydrogen,
$R_5$ is hydrogen,
$R_{11}$ is hydrogen; and
$R_{12}$ $C_1$–$C_4$alkyl.

Of special interest is a process for the preparation of 2,4-bis(n-octylthiomethyl)-6-methylphenol [Irganox 1520 (RTM), Ciba Specialty Chemicals] and of 2,4-bis(n-dodecylthiomethyl)-6-methylphenol.

The reaction of the compound of the formula II with formaldehyde and a compound of the formula III is carried out in the presence of mono- or dimethylamine or mono- or diethylamine as base. It is preferred to use dimethylamine as base. The base may be for example in the form of a 10–35% by weight solution in ethanol, methanol or another lower alcohol or in pure form. Dimethylamine can also be used in gaseous form.

The base can be used for example in an amount of 1 to 50 mol % and, most preferably, 5–20 mol %, based on the compound of the formula III.

The reaction of the compound of the formula II with formaldehyde and a compound of the formula III can be carried out in the presence of a solvent.

Examples of suitable solvents are alcohols of 1 to 6 carbon atoms, for example methanol, ethanol, propanol, butanol, pentanol or hexanol. However, it is also possible to use diols, polyols and ethers thereof, for example glycol, glycerol and polyethylene glycol. The reaction can be carried out in a polar aprotic solvent such as dimethylformamide or dimethylsulfoxide, or a high-boiling aromatic or aliphatic hydrocarbon or chlorinated hydrocarbon such as toluene, ligroin or chlorobenzene. The preferred solvent is dimethylformamide, which is diluted with one of the above mentioned lower alcohols or chlorinated hydrocarbons. It is preferred, however, to carry out the process in the absence of a solvent.

The reaction of the compound of the formula II with formaldehyde and a compound of the formula III can conveniently be carried out in the temperature range from 80° C. to 160° C., preferably from 90° C. to 150° C., and most preferably, from 90° C. to 130° C., and at normal pressure or under pressure (e.g. from 0.01 to 5 bar). In the absence of a solvent the reaction is preferably carried out under overpressure.

Depending on the specific compound of the formula II and compound of the formula III employed, the reaction times may vary and are for example from 1 to 24 hours and, preferably, from 1 to 6 hours. The reaction mixture is conveniently heated in a nitrogen atmosphere under reflux.

After cooling to room temperature, the reaction mixture is worked up by conventional separating and purifying methods.

Most of the compounds of the formula I, II and III are known and some are commercially available or can be prepared by known methods.

Formaldehyde or a compound that liberates formaldehyde under the reaction conditions, for example paraformaldehyde or hexamethylenetetramine, is used for the reaction. It is preferred to use formaldehyde, but paraformaldehyde is particularly preferred.

A preferred reducing agent is a hydride or hydrogen with a catalyst.

Preferred catalysts for hydrogenation are for example Pt, Pd, Rh, Ru, Ni like for example Raney-nickel, or Cu-Cr systems. The metals are supported on inert supports like for example carbon, alumina, barium sulfate. Especially preferred catalysts are Pt, Ru, Ni and Cu-Cr.

Of special interest is a process for the preparation of a compound of formula I wherein the reducing agent is a hydride.

Hydrides of special interest are for example sodium hydride, potassium hydride, calcium hydride, lithium aluminium hydride, aluminium hydride, sodium cyanoborohydride, sodium borohydride or diisobutylaluminium hydride. Preferred hydrides are sodium borohydride, sodium cyanoborohydride and diisobutylaluminium hydride.

Of very special interest is a process for the preparation of a compound of formula I wherein the reducing agent is sodium borohydride.

Advantageously, the reducing agent is used in an amount of from 0.02 to 10% by weight, especially from 0.02 to 1% by weight, e.g. from 0.07 to 0.5% by weight, based on the weight of the compound of the formula I.

The reaction step with a reducing agent can conveniently be carried out in the temperature range from 20° C. to 200° C., preferably from 40° C. to 150° C., and most preferably, from 60° C. to 100° C.

The reaction step with a reducing agent can be carried out in the presence of a solvent. Examples of suitable solvents are the same as mentioned above for the reaction of the compound of the formula II with formaldehyde and a compound of the formula III. It is preferred, however, to carry out the reduction step with a reducing agent in the absence of a solvent.

After cooling to room temperature, the reaction mixture is worked up by conventional separating and purifying methods.

The compounds of the formula I prepared by the process of this invention can be used as stabilisers for protecting organic materials from damage by the action of oxygen, heat, light or high-energy radiation. The preferred utility of these compounds is as antioxidants in organic polymers and in elastomers, or in mineral oils or synthetic lubricants.

The stabilisers are normally added to the organic materials in a concentration of 0.01 to 10% by weight, preferably 0.05 to 5.0% by weight, most preferably 0.1 to 2.0% by weight based on the organic material to be stabilised.

Incorporation of the compounds of the formula I can be effected, for example, by blending them with the material to be stabilised together with further optional additives by methods conventionally employed in the art, before or during the manufacture of articles shaped from said polymer, or also by applying the dissolved or dispersed compound to the polymer, with or without subsequent evaporation of the solvent. The compounds of the formula I may also be added to the materials to be stabilised in the form of a masterbatch which contains said compounds, for example, in a concentration of 2.5 to 25% by weight. In the case of cross-linkable polyethylene, the compounds are added prior to crosslinking.

In practice, the compounds of the formula I are added together with other stabilisers.

The compounds of the formula I are added to a rubber cement or latex preferably after polymerisation but prior to coagulation.

Lubricant formulations may also contain further additives which are added to improve certain use properties, for example further antioxidants, metal deactivators, rust inhibitors, viscosity index improvers, pour-point depressors, dispersants/surfactants and antiwear additives.

The following Examples illustrate the invention further. Parts or percentages relate to weight.

EXAMPLE 1

Preparation of 2,4-bis(n-octylthiomethyl)-6-methylphenol.

a) In a 1 liter reactor 84.2 g (2.81 mol) of para-formaldehyde, 134.9 g (1.25 mol) of o-cresol and 369.3 g (2.52 mol) of octhanethiol are charged. Then 9.9 g (0.22 mol) of dimethylamine is added. The temperature is then increased to 130° C. within one hour. The temperature is kept at 130° C. for 3.5 hours. The volatile constituents are then removed at a bath temperature of 90–95° C. under reduced pressure to give the crude 2,4-bis(n-octylthiomethyl)-6-methylphenol.

b) In a 500 ml flask, 390 g (0.92 mol) of crude 2,4-bis(n-octylthiomethyl)-6-methylphenol prepared according to Example 1a is mixed with 3.25 g of a caustic solution containing 12% of sodium borohydride, corresponding to 0.39 g (0.01 mol) of sodium borohydride. The mixture is heated at 90° C. for 7 hours. Afterwards the reaction mixture is extracted with acetic acid and water. The volatile constituents are then removed at a bath temperature of 90–95° C. under reduced pressure to give 380 g of 2,4-bis(n-octylthiomethyl)-6-methylphenol.

EXAMPLE 2

Preparation of 2,4-bis(n-octylthiomethyl)-6-methylphenol.

In a 500 ml flask, 410 g (0,97 mol) of crude 2,4-bis(n-octylthiomethyl)-6-methylphenol prepared according to Example 1a is mixed with 17 g of a caustic solution containing 12% of sodium borohydride; corresponding to 2.04 g (0.05 mol) of sodium borohydride. The mixture is heated at 90° C. for 7 hours. Afterwards, the reaction mixture is extracted with acetic acid and water. The volatile constituents are then removed at a bath temperature of 90–95° C. under reduced pressure to give 400 g of 2,4-bis(n-octylthiomethyl)-6-methylphenol.

EXAMPLE 3

Preparation of 2,4-bis(n-octylthiomethyl)-6-methylphenol.

In a 500 ml flask, 390 g (0,92 mol) of crude 2,4-bis(n-octylthiomethyl)-6-methylphenol prepared according to Example 1a is mixed with 1 g (0.026 mol) sodium borohydride. The mixture is heated at 90° C. for 7 hours. Afterwards, the reaction mixture is filtered and extracted with acetic acid and water. The volatile constituents are then removed at a bath temperature of 90–95° C. under reduced pressure to give 380 g of 2,4-bis(n-octylthiomethyl)-6-methylphenol.

EXAMPLE 4

Discoloration of mercaptomethylphenols in alkaline environment.

Various rubbers are polymerised in aliphatic organic solvents using n-butyl-lithium as catalyst/initiator (anionic polymerisation). After decomposition of the catalyst by means of water, lithium-hydroxide is formed as transition product. Thus the rubber cement is very alkaline as well as the water of the rubber coagulation system. Phenolic antioxidants are partly transformed under such conditions into the corresponding phenolates. Some of these phenolates or by-product phenolates have a yellow or orange colour. This discoloration leads to a yellow coloured rubber instead of a water white colourless rubber.

The tendency to discolour can be determined by a direct reaction of the phenolic antioxidant with the polymerisation initiator butyl-lithium. For this purpose 0.1 mmol n-butyl-lithium is added in form of a 10% solution in n-hexane to an equivalent amount of 2,4-bis(n-octylthiomethyl)-6-methylphenol dissolved in 100 ml n-hexane.

A sodium methylate treatment can be used as alternative method in order to avoid the use of butyl-lithium. 0.5 g of 2,4-bis(n-octylthiomethyl)-6-methylphenol according to Examples 1a, 1b, 2 and 3 were dissolved in 50 ml methanol; 0.5 g of a 10% solution of $NaOCH_3$ in methanol is added. The transmission of these solutions is measured at 300–500 nm using the UV-visible recording spectrophotometer Shimadzu UV-2100. The higher the transmission in % the better is the quality of the stabiliser. The results are summarised in Table 1. The discoloration can also be determined by measuring the yellowness Index. In this case, the sodium methoxide method was used with a quantity of 2.5 g 2,4-bis(n-octylthiomethyl)-6-methylphenol instead of 0.5 g. The yellowness index (YI) of the samples is determined in accordance with ASTM D 1925-70. Low YI values denote little discolouration, high YI values severe discoloration of the samples. The less discolouration, the more effective the stabiliser. The results are compiled in Table 1.

TABLE 1

| Examples | Stabiliser prepared according to | Transmission in % at 425 nm | Yellowness Index |
|---|---|---|---|
| Example 4a[a)] | Example 1a | 95.5 | 4.2 |
| Example 4b[b)] | Example 1b | 98.6 | 2.8 |
| Example 4c[b)] | Example 2 | 98.5 | 2.8 |
| Example 4d[b)] | Example 3 | 98.5 | 2.8 |

[a)]Comparison Example.
[b)]Examples of this invention.

What is claimed is:

1. A process for the preparation of a compound of the formula I (I)

wherein
n is 0 or 1,
$R_1$ is $C_1$–$C_{12}$alkyl or —$CH_2SR_3$,
$R_2$ is $C_1$–$C_{12}$alkyl, $C_7$–$C_9$phenylalkyl, $C_7$–$C_9$phenylalkyl substituted on the phenyl radical by from 1 to 3 $C_1$–$C_4$alkyl groups; or —$CH_2SR_3$,
$R_3$ is $C_6$–$C_{18}$alkyl, phenyl or benzyl,
$R_4$ is hydrogen or methyl,
$R_5$ is hydrogen or methyl, with the proviso that $R_4$ and $R_5$ are not simultaneously methyl, by reacting a compound of the formula II

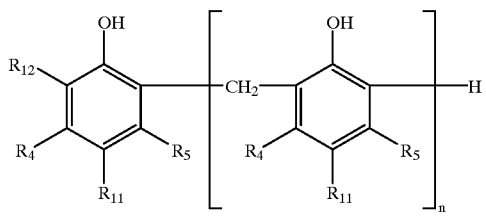 (II)

wherein
n, $R_4$ and $R_5$ are as previously defined,
$R_{11}$ is hydrogen or $C_1$–$C_{12}$alkyl; and
$R_{12}$ is hydrogen, $C_1$–$C_{12}$alkyl, $C_7$–$C_9$phenylalkyl, $C_7$–$C_9$phenylalkyl substituted on the phenyl radical by from 1 to 3 $C_1$–$C_4$alkyl groups, with formaldehyde or a compound that liberates formaldehyde under the reaction conditions and with at least one compound of the formula III $R_3SH$ (III)

wherein $R_3$ is as previously defined, in the presence of a base, said base being mono- or dimethylamine or mono- or diethylamine, which process comprises treating afterwards the reaction product with a hydride reducing agent.

2. A process according to claim 1, wherein
n is 0 or 1,
$R_1$ is $C_1$–$C_4$alkyl or —$CH_2SR_3$,
$R_2$ is $C_1$–$C_4$alkyl, $C_7$–$C_9$phenylalkyl, $C_7$–$C_9$phenylalkyl substituted on the phenyl radical by a methyl group,
$R_3$ is $C_6$–$C_{12}$alkyl,
$R_4$ is hydrogen or methyl,
$R_5$ is hydrogen,
$R_{11}$ is hydrogen or $C_1$–$C_4$alkyl; and
$R_{12}$ is $C_1$–$C_4$alkyl, $C_7$–$C_9$phenylalkyl, $C_7$–$C_9$phenylalkyl substituted on the phenyl radical by a methyl group.

3. A process according to claim 1, wherein
n is 0,
$R_1$ is —$CH_2SR_3$,
$R_2$ is $C_1$–$C_4$alkyl,
$R_3$ is $C_8$–$C_{12}$alkyl,
$R_4$ is hydrogen,
$R_5$ is hydrogen,
$R_{11}$ is hydrogen; and
$R_{12}$ $C_1$–$C_4$alkyl.

4. A process according to claim 1, wherein tha base is dimethylamine.

5. A process according to claim 1, wherein 1 to 50 mol % of base is used, based on the compound of the formula III.

6. A process according to claim 1, wherein the hydride is sodium borohydride.

7. A process according to claim 1, wherein the amount of reducing agent is 0.02 to 10% by weight based on the weight of the compound of the formula I.

8. A process according to claim 1, wherein the reaction is carried out in the absence of a solvent.

* * * * *